United States Patent
Schmued

(10) Patent No.: US 6,372,451 B1
(45) Date of Patent: Apr. 16, 2002

(54) HISTOCHEMICAL LABELING STAIN FOR MYELIN IN BRAIN TISSUE

(76) Inventor: Laurence C. Schmued, 200 Elizabeth Ann Dr., Pine Bluff, AR (US) 71602

( * ) Notice: Subject to any disclaimer, the term of this patent is extended or adjusted under 35 U.S.C. 154(b) by 0 days.

(21) Appl. No.: 09/840,628

(22) Filed: Apr. 23, 2001

Related U.S. Application Data
(60) Provisional application No. 60/199,290, filed on Apr. 24, 2000.

(51) Int. Cl.[7] ............................ G01N 1/30; G01N 33/48
(52) U.S. Cl. ........................ 435/40.5; 423/306; 423/312
(58) Field of Search ................................ 435/40.5, 306, 435/312

(56) References Cited

U.S. PATENT DOCUMENTS
6,229,024 B1   5/2001   Schmued

OTHER PUBLICATIONS

Gallyas F., Silver staining of myelin by means of physical development, Neurol. Res. 1 (1979) 203.

Hamilton, B. & Gould, D., Nature and distribution of brain lesions in rats intoxicated with 3–nitropropionic acid: a type of hypoxic energy deficient brain damage, Acta Neuropathol., 72 (1987) 286–297.

Kluver, H. and Barrera, E., Method for combined staining of cells and fibers in the nervous system,lJ. Neuropath, Exp. Neurol., 12 (1953) 400–403.

Kwon, O.S., Schmued, L., & Slikker, W. Fumonisin B1 in developing rats alters brain sphinganine levels and myelination, Neuro.Tox., 18 (1997) 571–580.

Lillie, R.D. & Fullmer, M. Histopathologic Technique and Practical Histochemistry, Mc–Graw Hill, New York, 1976, pp. 599–603.

Olney, J. Rhee, V., & Ho, O., Kainic acid: a powerful neurotoxic analogue of glutamate, Brain Res., 77 (1974) 507–515.

Quinn, B. & Graybiel, A., Myeloarchitectonics of the primate caudate–putamen, The Basal Ganglia IV, Plenum Press, 1994, 35–41.

Schmued L., Swanson L., and Sawchenko, P., Some useful fluorescent counterstains for neuroanatomical studies, J. Histochem. & Cytochem., 30 (1981) 123–128.

Schmued, L., & Fallon, J., "Fluoro–Gold" a new fluorescent retrograde axonal tracer with numerous unique properties, Brain Res., 377 (1986) 147–154.

Schmued, L., A rapid, sensitive histochemical stain for myelin in frozen brain sections, J. Histochem & Cytochem., 38 (1990) 717–720.

Schmued, L., Beltramino, C., and Slikker, W., Intracranial injection of Fluoro–Gold results in the degeneration of local but not retrogradely labeled neurons, Brain Res., 626 (1993) 71–77.

Schmued, L., Scallet, A., & Slikker, W., Domoic acid induced neuronal degeneration in the primate forebrain revealed by degeneration specific histochemistry, Brain Res., 695 (1995) 64–70.

Schmued, L., Albertson, C., Andrews, A., Sandberg, J., Nickols, J., & Slikker, W., Evaluation of brain and nerve pathology in rats chronically dosed with ddI or isoniazid, Neurotox. & Teratol., 18 (1996) 555–563.

Schmued, L., Albertson, C., & Slikker W., Fluoro–Jade: a novel fluorochrome for the sensitive and reliable localization of neuronal degeneration, Brain Res. 751 (1997) 37–46.

Weigert, C., Ausfurliche beschreibung der in No. 2 dieser Zeitschrift erwahnten neuen Farbungsmethode fur das centralnervensystem, Fortsch ritte der Medizin 2 (1884) 190–194.

Ciaccio, C., Contributo alla conscenza dei lipoidi cellulari, Ant. Anz., 35 (1909) 17.

*Primary Examiner*—Jean C. Witz
*Assistant Examiner*—Brett Ozga
(74) *Attorney, Agent, or Firm*—Ralph F. Crandell

(57) ABSTRACT

A novel aurophosphate stain for staining a slide-mounted brain tissue slice or section to label myelin therein, the method of staining, and the method of making the stain. The stain is potassium aurophosphate or sodium aurophosphate produced as the reaction product of an aurochloride and a dibasic potassium or sodium phosphate. Slide-mounted brain tissue slices are stained by immersing the slice in a warn solution of the aurophosphate. The stained slice may be intensified by immersing the slide-mounted stained tissue slice in a potassium tetrachloroaureate solution. The stained or intensified slice can be fixed by immersion in a sodium thiosulfate solution. Large bundles of stained myelin appear deep red-brown, while smaller bundles and individual fibers appear black.

23 Claims, 3 Drawing Sheets

(3 of 3 Drawing Sheet(s) Filed in Color)

US 6,372,451 B1

HISTOCHEMICAL LABELING STAIN FOR MYELIN IN BRAIN TISSUE

CROSS REFERENCE TO RELATED APPLICATIONS

This application claims the benefit of Provisional Application Ser. No. 60/199,290, filed Apr. 24, 2000, by Laurence C. Schmued, for Histochemical Label for Myelin in Brain Tissue.

GOVERNMENT CONTRACT RIGHTS

This invention was made with Government support and was funded by FDA protocol #7013.01. The portion involving isoniazid induced myelinopathy was funded by NIEHS interagency agreement (Y01-ES-10187). The Government may have certain rights in this invention.

BACKGROUND OF THE INVENTION

1. Field of the Invention

The present invention relates to a histochemical stain, a method for producing the stain, and a method for the post-mortem detection and localization of myelin in brain tissue slices.

2. Description of the Prior Art

On the most fundamental level, the brain can be divided into two distinctly different appearing types of matter, the white matter and the gray matter. In recent years, numerous histochemical techniques have been developed for the localization of neuronal and astrocytic markers within the gray matter. Fewer markers, however, are available to the researcher studying the myelin which comprises the white matter. Existing methods for staining myelin include those based on lipid solubility such as Sudan black or Oil red O, the affinity for non-solvent extractable phospholipids by Luxol Fast Blue, the chelation of complex lipid polymers with potassium dichromate followed by hematoxylin, the suppression of non-myelin argyrophilia with pyridine followed by diamine silver, the immunohistochemical localization of myelin basic protein, and the use of aqueous gold chloride solutions.

The use of gold salts as a myelin stain has a long and controversial history. The use of gold chloride as a sensitive myelin stain is known in the art. The use of gold chloride in hypotonic phosphate buffered saline to study the myelinopathy resulting from exposure to isoniazid or fumonisin indicates that although the gold chloride based method has the potential to detect myelin pathologies, it, like the previous gold chloride based methods, also suffered from a certain degree of capriciousness.

OBJECTS OF THE INVENTION

The principal object of the present invention is to provide a stable, soluble, gold based complex stain which retains the advantages associated with the traditional gold chloride stains and methods while eliminating the drawbacks associated therewith.

Another object of the invention is to provide a stain of the foregoing character for simply and sensitively labeling normal and pathological myelin in brain tissue sections.

A further object of the invention is to provide a stain of the foregoing character which is consistent in results and affords relatively short staining times.

SUMMARY OF THE INVENTION

In accordance with the foregoing objects, the novel histochemical marker or stain embodying the present invention was synthesized and was applied as a stain or label to demonstrate both normal and pathological myelin. This stain is identified as a aurophosphate complex, more specifically a potassium aurophosphate, $[K_6Au(PO_4)_3]_n$, produced as the reaction product of dibasic potassium phosphate and a gold chloride.

To examine pathological myelin changes, a number of agents known to cause brain damage were used including isoniazid, 3-nitropropionic acid, kainic acid, domoic acid, and intracranial injection of amidino stilbene.

DESCRIPTION OF THE DRAWINGS

The file of this Patent contains at least one drawing executed in color. Copies of this patent with color drawings will be provided by the Office upon request and payment of the necessary fee.

A: Low magnification of hippocampus and surrounding brain tissue stained with the stain of the present invention without post-intensification; magnification bar= 1.25 mm.

B: High magnification view of the dentate gyrus region of the hippocampus showing staining of individual myelinated fibers without post-intensification; magnification bar=84 um.

C: Low magnification of hippocampus and dorsal cortex following treatment with the stain of the present invention and post-intensification with potassium tetrachloroaureate; magnification bar=1.25 mm.

D: High magnification of the dentate gyrus stained with Black-Gold stain of the present invention old followed by post-intensification; magnification bar=84 um.

E: Survey view of the normal rat brain reveals a pallor in myelin free areas, fine dark individual myelinated fibers in neuropil regions, and the red brown staining of large myelinated tracts such as the corpus callosum and the internal capsule; magnification bar=2.5 mm.

F: High magnification photograph of the CA-1 region of the hippocampus photographed with dark field optics, giving the regions stained with the stain of the present invention a yellow appearance; magnification bar=0.58 mm.

G: Myelinated fibers of the cortex appear to radiate out from the corpus callosum at lower left; magnification bar=0.29 mm.

H: Within the striatum, both large condensed bundles of myelinated fibers and thin individual myelinated fibers can be visualized with the stain of the present invention; magnification bar=0.29 mm.

Figure 2:
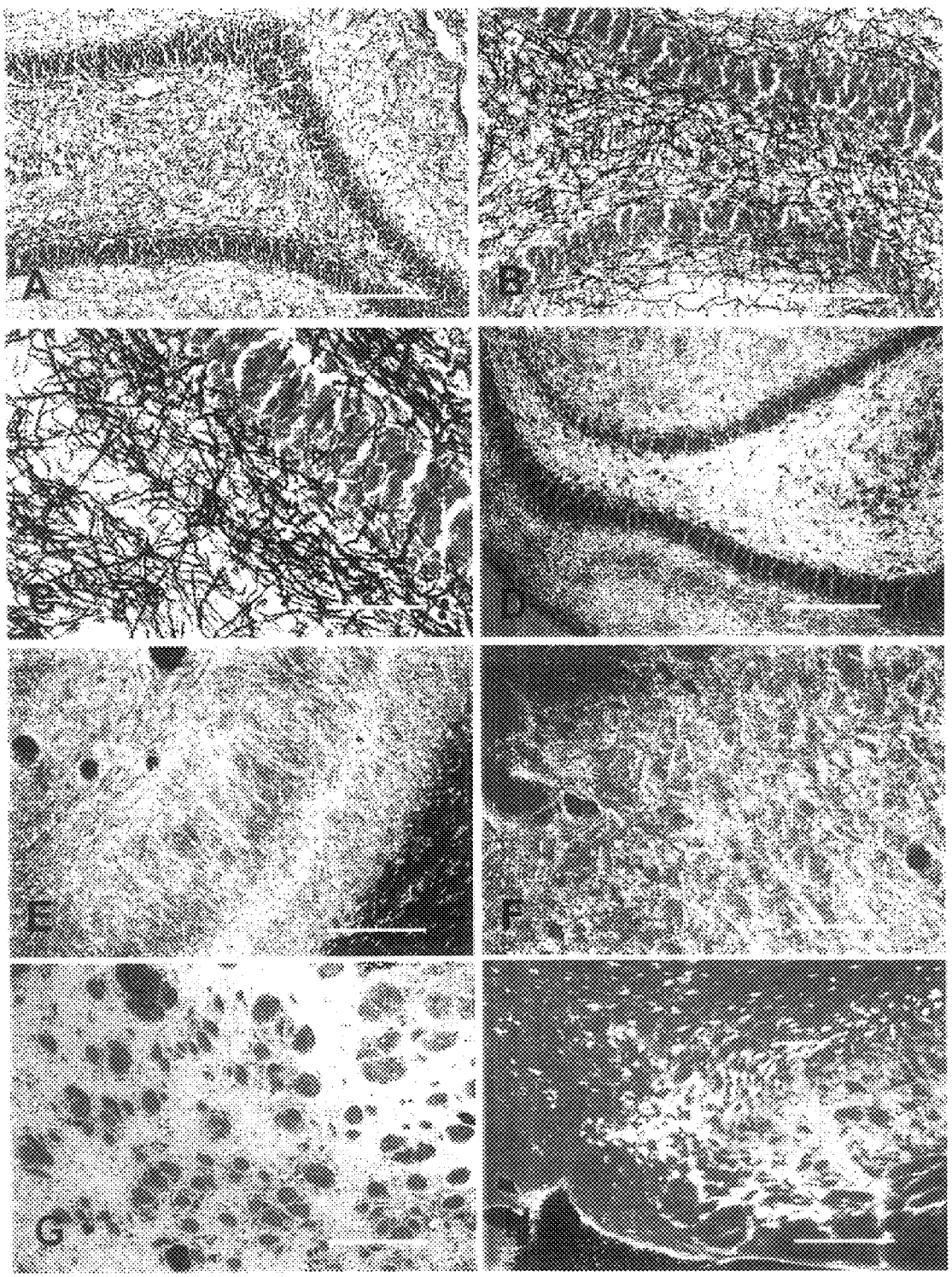

FIG. 2 is a set of eight color photomicrographs showing staining of rat brain tissue sections with multiple stains including the stain of the present invention and wherein the photomicrographs show:

A: Low magnification of the dentate gyrus in which granule and polymorph cells are stained with cresyl violet acetate and the myelin is stained with the stain of the present invention; magnification bar=168 um.

B: Intermediate magnification of Ammon's horn in which pyramidal cells are stained with malachite green and myelinated fibers are stained with the stain of the present invention; magnification bar=84 um.

C: High magnification of the CA-1 region of the hippocampus in which pyramidal cells are stained with neutral red and the myelinated fibers are stained with the stain of the present invention; magnification bar=42 um.

D: Dark field illumination of the dentate gyrus stained with malachite green and the stain of the present invention results in dark blue cells and gold colored myelinated fibers; magnification bar=168 um.

E: Combined dark field and ultraviolet epifluoresencent illumination reveal the hippocampal myelin within the CA-1 region labeled by the stain of the present invention and DAPI staining of neuronal and astrocytic cell bodies; magnification bar=169 um.

F: Combined dark field and blue light epifluorescent illumination allows visualization of both fragmented myelin (1) labeled by the stain of the present invention and carboxyfluorescein homologue labeled positive degenerating neurons, 24 hours after exposure to kainic acid; magnification bar=84 um.

G: Combined dark field and ultraviolet epifluorescent illumination of the striatum reveals an amidino stilbene labeled injection site (upper right) which is devoid of the fine myelinated fibers seen surrounding it, although large myelinated fascicles are seen in both areas; magnification bar=169 um.

H: Combined dark field and ultraviolet epifluoresence reveals the myelination of the midbrain relative to the white appearing substantia nigra cells retrogradely labeled by a fluorescent amidino stilbene compound from the injection site seen in the previous figure; magnification bar=168 um.

Figure 3:
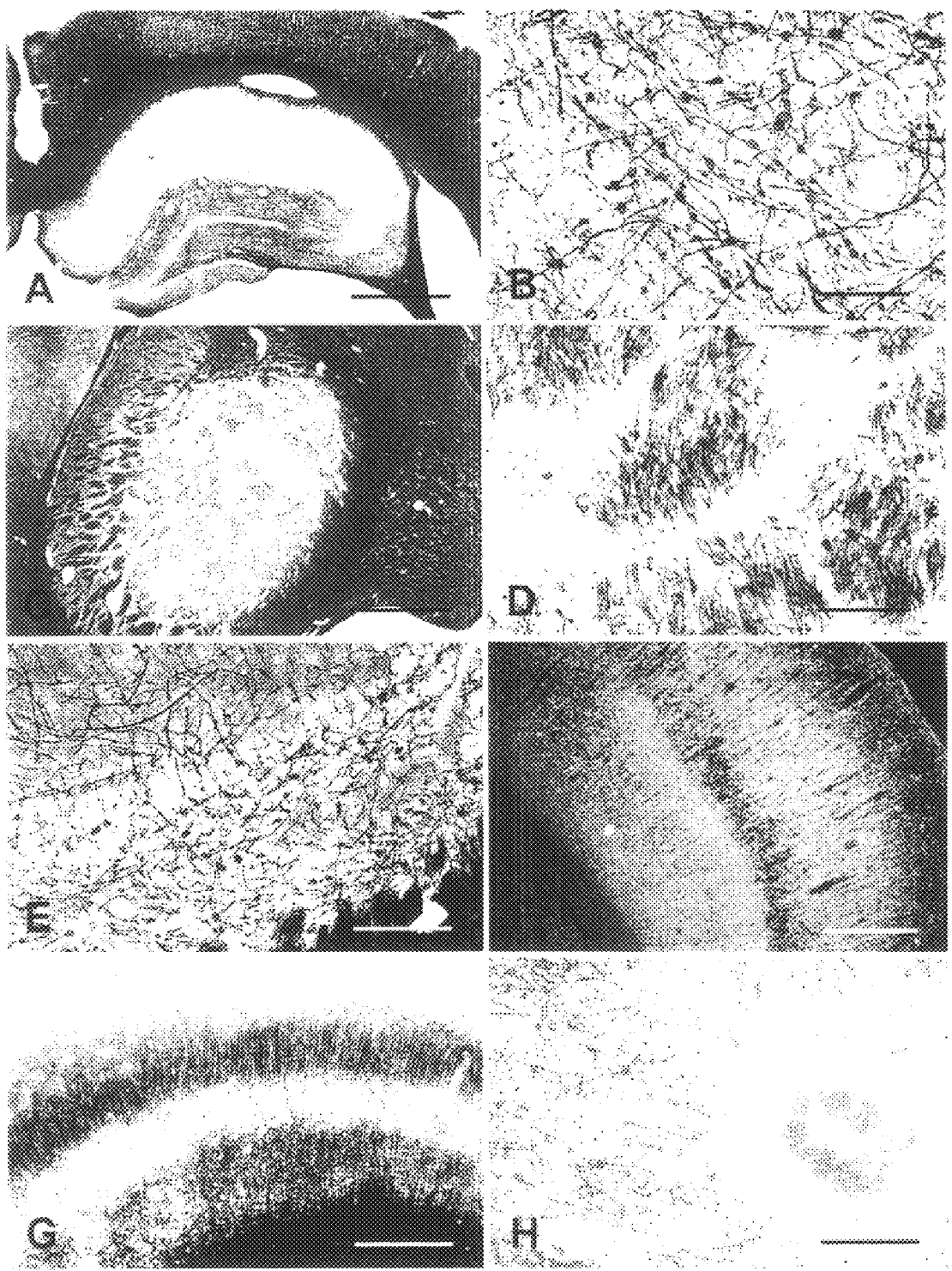

FIG. 3 is a set of eight color photomicrographs showing staining of neurotoxicant induced pathologies in rat brain tissue sections with the stain of the present invention and wherein the photomicrographs show:

A: The hippocampus and dorsal cortex of an animal dosed with kainic acid one week prior to sacrifice. Normal myelination is seen in the cortex and dentate gyrus but the myelin is virtually absent throughout Ammon's horn; magnification bar=1.25 mm.

B: High magnification of the hilus of the dentate gyrus 24 hours after exposure to kainic acid reveals myelinated fibers with "bead-like" varicosities; magnification bar= 42 um.

C: Survey view of the striatum of an animal given 3-nitropropionic acid one week before sacrifice reveals an almost complete lack of myelin; magnification bar= 1.25 mm.

D: High magnification of the striatum seen in the previous figure reveals an absence of fine myelinated fibers and a disaggregation of the large penetrating myelin fascicles; magnification bar=84 um.

E: CA-1 region of the hippocampus of an animal given domoic acid 24 hours prior to sacrifice shows both fragmented and varicose myelin; magnification bar=84 um.

F: Dark field illumination of parietal cortex following a 20 week exposure to isoniazid reveals demyelination throughout layer IV; magnification bar=0.55 mm.

G: The sensory/motor cortex after a 20 week exposure to isoniazid reveals demyelination in layers IV and V; magnification bar=0.55 mm.

H: A blood clot is seen at the center of an amidino stilbene labeled injection site in the hippocampus. The immediate surround is devoid of myelin staining while. fragmented and varicose fibers can be seen more peripherally; magnification bar=84 um.

DESCRIPTION OF THE INVENTION

The present invention is embodied in a histochemical stain, specifically an aurophosphate histochemical stain, a method for making the aurophosphate stain, and the method of staining brain tissue slices or sections to label normal and pathological myelin. The aurophosphate labeling stain embodying the present invention is the unique compound $[K_6AU(PO_4)_3]_n$ where n is an integer from 1 to infinity and indicates polymerization. This compound is produced by mixing 1 mole of potassium tetrachloroaureate and 3 moles of dibasic potassium phosphate and recovering the aurophosphate produced. More specifically, this compound is produced by mixing equal volumes of a 0.3M solution of dibasic potassium or sodium phosphate and a 0.1M solution of gold chloride, hydrogen gold chloride, sodium gold chloride or potassium gold chloride. It should be noted that the use of the potassium or sodium salt of gold chloride will also generate one molecule of the respective simple salt (e.g. NaCl or KCl) which may be incorporated into the aurophosphate complex. The solutions are mixed together for 20 minutes at 60 degrees Centigrade. Over this time the solution changes from a deep yellow to a pale yellow color. Water is then removed either by evaporation or freeze drying. The resulting dehydrated aurophosphate precipitate is then pulverized and stored in a desiccator. Should sodium phosphate be used, then the Na salt instead of the K salt is produced. The compounds $[K_6Au(PO_4)_3]_n$ and $[Na_6Au(PO_4)_3]_n$ embodying the present invention will be referred to herein as potassium aurophosphate or sodium aurophosphate, or sometimes more generally as aurophosphate.

The compound $[K_6Au(PO_4)_3]_n$ or potassium aurophosphate is utilized for staining brain tissue sections to label the myelin by reconstituting the solids into a solution. To this end, a 0.2% solution is made by adding 100 milligrams of the compound to 50 ml of 0.9% NaCl and then heating it to 60° C. The solution is preferably heated in a microwave oven to the approximate temperature, and then allowed to fully equilibrate to 60° C. in a conventional oven. When stored in the dark, both impregnation and intensification solutions remain stable and useable for at least two months.

For staining, slide mounted tissue sections or slices are transferred to a warm aurophosphate stain impregnating solution in the oven for 12–18 minutes. As the exact staining time will vary depending on section thickness and solution temperature, it is advisable to initially monitor the staining visually. The sections are typically examined microscopically after 12 minutes. Staining of the fine parallel fibers of the molecular layer of the cortex is a good indicator of proper impregnation. If the section is under impregnated these fibers will not be visible, indicating that the section should be placed in the aurophosphate staining solution again and microscopically examined at two or three minute intervals. If the section is left in the staining solution too long it will become over impregnated allowing the neuropil in the molecular layer to acquire a lavender background color.

At this point it is possible to intensify the stain by incubating the sections for 10–15 minutes in a 0.2% potassium tertachloroaureate solution at a temperature of about 60° C. The potassium tetrachloroaureate is obtainable from Aldrich Chemical Company, Inc., Milwaukee, Wis., and is dissolved in 0.9% saline solution. The intensified or non-intensified sections are then rinsed for 2 minutes in distilled water, fixed for 3 minutes in a 2% sodium thiosulfate solution, and then rinsed in tap water for at least 15 minutes using three 5 minute changes. Slides are either air dried on a slide warmer or dehydrated through gradated alcohols. The dehydrated sections are cleared in xylenes for at least two minutes and then cover-slipped with commercially available plastic mounting media.

All experiments utilized adult (3–6 month old) Sprague-Dawley rats. Food and water were given ad libitum. Five groups of animals, with ten animals per group, received five different respective treatments. One additional group consisted of control animals that were not exposed to any neurotoxicants. Unless indicated otherwise, all neurotoxicants were obtained from Sigma Chemical Company (St. Louis, Mo.) and were delivered via a single i.p. injection one or seven days prior to sacrifice. The following five neurotoxicants were administered at the following respective doses: 1) kainic acid [10 mg/kg]; 2) domoic acid [1.3 mg/kg]; 3) 3-nitropropionic acid [30 mg/kg, s.c.]; 4) isoniazid [80 mg/kg given daily by oral gavage for 20 weeks prior to sacrifice], and 5) 0.1 ul of 5% Fluoro-Gold [Fluorochrome Inc, Denver Colo.] injected stereotaxically into the striatum.

All animals were anesthetized with Retamine (75 mg/kg) and Rompun (9 mg/kg) and then perfused with 500 ml of 0.1 M neutral phosphate buffered 10% formalin (4% formaldehyde) via the ascending aorta. The brains were post-fixed at least overnight in the same fixative solution. Twenty percent sucrose was added to the post-fixation solution of those brains that were to be cut on a freezing sliding microtome. Either frozen sections or vibratome sections were cut at a thickness of 20–50 microns and collected in 0.1 M neutral phosphate buffer. The sections were then typically mounted on (2%) gel coated slides and then air dried on a slide warmer (at 50° C.) for at least ½ hour. The sections can be stained loose, although the sections are easier to handle when mounted on slides. The mounted sections were rehydrated in distilled water for two minutes before transferring them to the warm stain solution as described above.

Once the myelin staining is complete and before the tissue has been dehydrated or cleared, it can be labeled with any number of counterstains to provide multiple labels. Nissl stains can be used to localize cell bodies relative to myelin. To achieve this end, sections were stained for 5 minutes in a 0.1% acetic acid solution containing either 0.1% cresyl violet acetate, 0.2% neutral red, or 0.4% malachite green. These dyes (available from Aldrich Chem Co., St. Louis, Mo.) respectively resulted in the violet, red, or green/blue staining of cell bodies. After staining, the sections were rinsed for one minute in distilled water, differentiated in 70% alcohol until most of the background neuropil is destained, and dehydrated by immersing the slides for one minute in 95% alcohol followed by two one minute changes of 100% alcohol. The sections are then cleared in xylenes and coverslipped.

Many fluorescent nucleic acid stains can be used as fluorescent Nissl stains [11]. Two such stains are DAPI [4,6-diamidino-2-phenylindole] and ethidium bromide (Aldrich Chem. Co., St. Louis, Mo.) which respectively result in blue or red appearing cells under ultraviolet or green light epi-illumination. This illumination was typically combined with dark field visualization of the potassium aurophosphate stain to provide optimal co-localization of both tracers. For all studies requiring dark field optics, an annular dark field condenser and objective lenses with numerical apertures of less than 0.8 were used. The staining was achieved by incubating the potassium aurophosphate stained tissue sections for 5 minutes in a solution of 0.0002% DAPI or ethidium bromide in 0.1% acetic acid. The sections were then rinsed in three one minute changes of distilled water, air dried, xylene cleared and then coverslipped with D.P.X.

Another group of animals received an intracranial stereotaxic injection (0.1 ul of a 5% solution) of the fluorescent retrograde axonal tracer Fluoro-Gold into the striatum either one week or one day before sacrifice. The subsequent histochemical processing was identical to that described for potassium aurophosphate alone. The two tracers are best co-localized by combining epifluorescent illumination with conventional dark field illumination.

When evaluating brain pathology, it may be of value to simultaneously look for both myelin and neuron pathologies. This can be achieved by counterstaining the potassium aurophosphate with an anionic fluorescein as described in my Application Ser. No. 09,234,766, filed Jan. 21, 1999, for Method For Detecting Neuronal Degeneration and Anionic Fluorescein Homologue Stains Therefor, now U.S. Pat. No. 6,229,024. These stains are available under the trademarks Fluoro-Jade and Fluoro-Jade B from Histo-Chem, Inc. of Jefferson, Ariz. Briefly, potassium aurophosphate stained sections were incubated for 30 minutes at room temperature in a solution of 0.0002% Fluoro-Jade or Fluoro-Jade B dissolved in 0.1% acetic acid. The sections were then rinsed for three minutes in each of three changes of distilled water, air dried on a slide warmer, cleared in xylene and coverslipped with D.P.X. mounting media. As with other combined fluorescent methodologies, the two tracers are best visualized by combining dark field illumination with epifluorescent illumination (blue light excitation).

Figure 1:
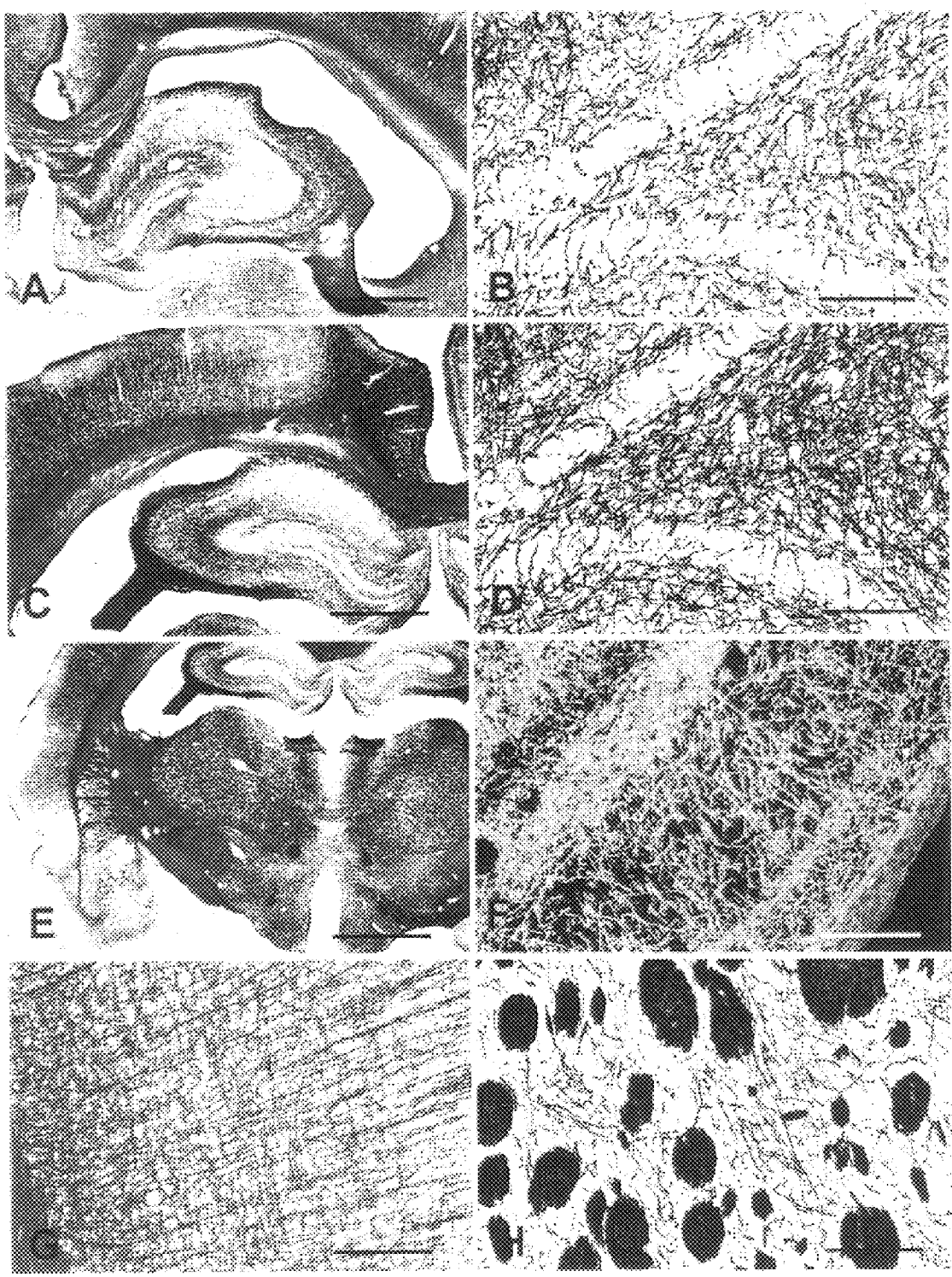
FIG. 1 is a set of eight color photomicrographs showing staining of rat brain tissue sections with the stain of the present invention and wherein the photomicrographs show.

The myelin stain develops progressively when the section is transferred to the warm potassium aurophosphate solution. After about five minutes in this impregnating solution, large myelinated tracks like the corpus callosum and internal capsule appear pale red. Over the next five-ten minutes, fine myelinated fibers become visible (FIGS. 1A, 1B). Optimum impregnation of the cortex (FIG. 1G), for example, will result in the corpus callosum appearing a medium red-brown, bundles of radially oriented myelinated fibers appear dark red-brown, while individual parallel myelinated fibers in the molecular layer appear virtually black. Over impregnation can result in background staining of the neuropil which should remain colorless. Post-impregnation intensification for 10–15 minutes in warm potassium tetrachloroaureate results in large bundles of myelin appearing deep red-brown while smaller bundles and individual fibers appear black (FIGS. 1C, 1D, 1E, and 1H).

Dark field illumination results in individual myelinated fibers appearing a golden color against a virtually black background while large tracts containing many myelinated axons appear brown (FIGS. 1F, 3F). Neurons counterstained with malachite green appear dark blue under darkfield illumination (FIG. 2D).

Counterstained sections result in staining of the cytoplasmic Nissl substance of cell bodies within the brain. Thus, counterstaining myelin stained sections with cresyl violet acetate (FIG. 2A), malachite green (FIG. 2B), or neutral red (FIG. 2C) result in the respective violet, blue-green, or red staining of neurons and other types of cells when viewed under bright field illumination. Sections stained with the fluorescent Nissl stains ethidium bromide or DAPI result in the respective red or blue staining of intact cells under epifluorescent illumination (FIG. 2E).

Exposure to glutamate receptor agonists results in a similar pattern of conspicuous changes in the morphology of individual myelinated fibers in certain brain regions. These regions typically correspond to those regions which have been shown to undergo neuronal degeneration using suppressed silver or Fluoro-Jade methods. Most severely altered are the hippocampal complex, except for granule cells (FIGS. 2F, 3A, 3B), the piriform cortex and the medial and dorsal thalamic nuclei. The animals dosed with domoic acid showed a similar pattern of myelin changes especially apparent in the efferent projections of these structures. For example, extensive hippocampal damage results in dramatic myelin changes within the lateral septum. The changes typically consist of varicosities along the myelin sheath, giving them the appearance of a string of beads (FIG. 3B). These varicosities are especially prominent in the aforementioned brain regions at 24 hours post drug exposure. In animals exposed for longer intervals (e.g. 7 days), the myelin often appears fragmented (FIG. 3E) or absent (FIG. 3A) implying extensive hypomyelination of the most affected areas.

3-nitropropionic acid, an inhibitor of oxidative respiration results in massive myelin changes in brain regions previously shown to contain degenerating neurons with silver or Fluoro-Jade methods. Thus, the striatum, the thalamus, and the deep nuclei of the cerebellum are most adversely affected. The efferent projections of these areas also exhibit degeneration of myelinated axons. For example, degeneration within deep nuclei of the cerebellum also reveals conspicuous myelin changes associated with axons in the superior cerebellar peduncle and the red nucleus, while striatal lesions were associated with myelin changes in the endopeduncular nucleus and the substantia nigra pars reticulata. Low power examination of the striatum reveals a large pallid region (FIG. 3C). High power examination of this region (FIG. 3D) reveals that the dispersed penetrating fibers appear pale, disaggregated and contain some varicosities. The fine intrinsic myelinated fibers seen in normal tissue are virtually absent in the lesioned area. Myelin staining in the thalamus and deep cerebellar nuclei is also more pallid, and axon fragmentation is apparent.

After 20 weeks of oral dosing with isoniazed, extensive cortical lesions are observed. One striking feature seen at low magnification is the differential staining according to lamina (FIG. 3G). Myelin staining is most conspicuous in cortical layers III and VI, while virtually absent in layers I, IV, and V. High magnification examination of the border between layers VI and V reveals fragmented myelin and the presence of macrophage-like round structures which appear to contain labeled fragments of myelin.

Dye and clotted blood cells can be seen at the core of the Fluoro-Gold intracranial injection site (FIGS. 2G, 3H). Surrounding this region is a pallid penumbra which is completely devoid of myelin staining. Peripheral to this region is a tertiary zone in which myelin is present, but with conspicuous varicosities and puncta. In the midbrain, cells labeled with Fluoro-Gold via retrograde axonal transport can be seen relative to normal appearing myelin (FIG. 2H).

Potassium aurophosphate embodying the present invention is an effective histochemical stain for myelin in formalin fixed non-embedded brain tissue sections. Although the exact histochemical mechanism underlying this staining technique is not fully understood, it is probable that solvent extractable lipids in myelin, combined with formaldehyde fixation, are capable of reducing the water soluble potassium aurophosphate. In many ways this is similar to the gold chloride in hypotonic phosphate buffered saline method. It differs, however, in three key ways: 1) substitution of potassium aurophosphate $[K_6Au(PO_4)_3]_n$, a stable water soluble aurophosphate complex, for the hygroscope gold chloride and sodium phosphate reagents, greatly increases the reliability and reproducibility of the technique; 2) post-treatment with potassium tetrachloroaureate further intensifies and darkens the stain; and 3) increasing the temperature of the staining solution to 60° C. reduces the staining time by approximately an order of magnitude, from two hours to about 15 minutes.

The potassium aurophosphate staining solution of the present invention shows no detectable precipitation after intermittent use for a month. After a month, a fine dark precipitate becomes detectable in the bottom of coplin jars. Even several months after the appearance of such a precipitate, one can still obtain high quality staining by simply increasing the incubation time by one or two minutes. The working life of the potassium aurophosphate staining leg solution is maximized by avoiding extended exposure to bright light, especially direct sunlight.

Potassium aurophosphate can be used for either neuroanatomical or neuropathological studies. Researchers studying normal brains can employ this method to examine the morphology and distribution of large myelinated fascicles as well as fine individual myelinated fibers. Researchers interested in neurotoxicology and neuropathology can also use this method in several ways. One way is to infer demyelination by the absence of potassium aurophosphate staining compared to control brains. A second way is to study morphological changes in the myelin such as a fragmented or beaded appearance of the myelin sheath. The technique can also be used to show some secondary changes such as the internalization of stained myelin fragments by macrophages in sections from animals chronically dosed with certain neurotoxicants such as isoniazid.

The advantages associated with the use of potassium aurophosphate on formaldehyde fixed tissue include the highest resolution and the highest contrast staining of fine individual fibers and fascicles of any technique. The technique is also faster than conventional techniques. Potassium aurophosphate is also superior to previous gold-based myelin stains as it does not share their capricious staining properties. This consistency is significant as a lack of reproducibility has ultimately precluded the widespread acceptance of previous gold based myelin stains. Reproducible staining requires proper tissue storage prior to staining. Specifically, tissue sections should be stored in isotonic neutral or basic buffer solution and should not be stored air dried on slides or in solutions containing formaldehyde. The primary limitation of the technique is that it is not applicable to unfixed (e.g. fresh cryostat) or solvent extracted (e.g. paraffin embedded) tissue sections. Compared to conventional myelin stains, potassium aurophosphate is used at much lower concentrations and may be reused many times when stored properly. The aforementioned attributes make potassium aurophosphate an ideal candidate for the localization of both fine, normal myeloarchitectonics as well as relatively subtle disease and neurotoxicant induced myelin changes.

What is claimed is:
1. $[K_6Au(PO_4)_3]$.
2. $[K_6Au(PO_4)_3]_n$ where n is an integer.
3. $[Na_6Au(PO_4)_3]$.
4. An aurophosphate histochemical stain produced by the process comprising the steps of combining 1 mole of potassium tetrachloroaureate and 3 moles of dibasic potassium phosphate and recovering the aurophosphate stain as a precipitate.
5. An aurophosphate histochemical stain produced by the process comprising mixing for 20 minutes at 60 degrees

Centigrade equal volumes of a 0.3M solution of a dibasic phosphate selected from the group consisting of potassium phosphate and sodium phosphate, and a 0.1M solution of an aurochloride selected from the group consisting of gold chloride, hydrogen gold chloride, sodium gold chloride and potassium gold chloride; and dehydrating said solution to remove water therefrom and produce a solid aurophosphate precipitate.

6. An aurophosphate histochemical stain as defined in claim 5 wherein said water is removed by heating and maintaining said solution at about 40° C.

7. An aurophosphate histochemical stain as defined in claim 5 wherein said water is removed by freeze drying.

8. An aurophosphate histochemical stain as defined in claim 5 wherein said solid precipitate is pulverized and stored in a desiccator at room temperature.

9. An aurophosphate histochemical stain as defined in claim 5 wherein said phosphate is potassium phosphate.

10. An aurophosphate histochemical stain as defined in claim 5 wherein said aurochloride is potassium gold chloride.

11. An aurophosphate histochemical stain produced by the process comprising mixing for 20 minutes at 60 degrees Centigrade equal volumes of a 0.3M solution of a dibasic phosphate selected from the group consisting of potassium phosphate and sodium phosphate, and a 0.1M solution of an aurochloride selected from the group consisting of gold chloride, hydrogen gold chloride, sodium gold chloride and potassium gold chloride; dehydrating said solution by evaporation or freeze drying to produce a solid precipitate; pulverizing said precipitate; and storing said precipitate in a desiccator.

12. A method of producing an aurophosphate histochemical stain comprising mixing for 20 minutes at 60 degrees Centigrade equal volumes of a 0.3M solution of a dibasic phosphate selected from the group consisting of potassium phosphate and sodium phosphate, and a 0.1M solution of an aurochloride selected from the group consisting of gold chloride, hydrogen gold chloride, sodium gold chloride and potassium gold chloride; dehydrating said solution by evaporation or freeze drying to produce a solid precipitate; pulverizing said precipitate; and storing said precipitate in a desiccator.

13. A method of staining a brain tissue slice to label myelin therein comprising forming an aurophosphate histochemical stain by the steps comprising mixing for 20 minutes at 60 degrees Centigrade equal volumes of a 0.3M solution of a dibasic phosphate selected from the group consisting of potassium phosphate and sodium phosphate, and a 0.1M solution of an aurochloride selected from the group consisting of gold chloride, hydrogen gold chloride, sodium gold chloride and potassium gold chloride; dehydrating said solution by evaporation or freeze drying to produce a solid precipitate; pulverizing said precipitate; mixing said precipitate with a saline solution in an amount sufficient to form a 0.2% solution; heating said solution to about 60 degrees Centigrade; and immersing a slide-mounted brain tissue slice in said warm solution for a time sufficient to label the myelin therein.

14. A method of staining a brain tissue slice to label myelin therein comprising mixing a pulverized solid aurophosphate stain compound with a saline solution in an amount sufficient to form a 0.2% solution of said stain; heating said solution to about 60 degrees Centigrade; and immersing a slide-mounted brain tissue slice in said warm solution for a time sufficient to label the myelin therein.

15. A method of staining a brain tissue slice to label myelin therein comprising immersing a slide-mounted brain tissue slice in warm aurophosphate stain solution for a time sufficient to label the myelin therein.

16. A method of staining a brain tissue slice as defined in claim 13, 14, or 15 further comprising intensifying the stain by immersing and incubating the stained tissue slice in a 0.2% potassium tetracholroaureate solution.

17. A method of staining a brain tissue slice as defined in claim 16 further comprising fixing the intensified stain by immersing the stained tissue slice in a 2% sodium thiosulfate solution.

18. A method of staining a brain tissue slice as defined in claim 16 further comprising rinsing said stained slice in distilled water, fixing the intensified stain by immersing the stained tissue slice in a 2% sodium thiosulfate solution, rinsing the fixed stained slice in tap water, and drying the slide to dehydrate the tissue slice.

19. A method of staining a brain tissue slice as defined in claim 13, 14, or 15 further comprising fixing the stain by immersing the slide-mounted slice in a 2% sodium thiosulfate solution.

20. A method of staining a brain tissue slice as defined in claim 13, 14, or 15 further comprising rinsing said slide-mounted stained slice in distilled water, fixing the stain by immersing the stained tissue slice in a 2% sodium thiosulfate solution, rinsing the fixed stained slice in tap water, and drying the slide to dehydrate the tissue slice.

21. A method of staining a brain tissue slice as defined in claim 13, 14, or 15 further comprising counterstaining said slide-mounted brain tissue slice with a counterstain.

22. A method of staining a brain tissue slice as defined in claim 21 wherein said counterstain comprises a fluorescent stain.

23. A method of staining a brain tissue slice as defined in claim 21 wherein said counterstain comprises a fluorescent retrograde axonal tracer.

* * * * *